US005458886A

United States Patent [19]

Briquet

[11] Patent Number: 5,458,886

[45] Date of Patent: Oct. 17, 1995

[54] ANTIFOAM COMPOSITIONS

[75] Inventor: Francois J. Briquet, Nice, France

[73] Assignee: Dow Corning France S.A., Valbonne, France

[21] Appl. No.: 251,436

[22] Filed: May 31, 1994

[30] Foreign Application Priority Data

Jun. 4, 1993 [FR] France .................................. 93 06695

[51] Int. Cl.$^6$ .............................. A61K 9/48; A61K 9/26; A61K 9/16; A61K 9/46

[52] U.S. Cl. .......................... 424/451; 424/456; 424/465; 424/466; 424/470; 424/501; 514/819; 514/820; 514/925

[58] Field of Search .................................. 424/466, 464, 424/474, 475, 451, 456, 465, 470, 501; 514/819, 820, 925

[56] References Cited

U.S. PATENT DOCUMENTS

| | | | |
|---|---|---|---|
| 2,441,098 | 5/1948 | Hyde | 260/607 |
| 4,115,553 | 9/1978 | Rubino | 424/155 |
| 4,906,478 | 3/1990 | Valentine et al. | 424/682 |
| 5,073,384 | 12/1991 | Valentine et al. | 423/877 |

FOREIGN PATENT DOCUMENTS

| | | | |
|---|---|---|---|
| 985546 | 3/1965 | United Kingdom . | |
| 1019353 | 2/1966 | United Kingdom . | |
| 1051687 | 12/1966 | United Kingdom | C08G 47/02 |
| 1051688 | 12/1966 | United Kingdom | C08G 47/02 |
| 1079832 | 8/1967 | United Kingdom | C08G 47/02 |
| 1110207 | 4/1968 | United Kingdom | C08G 47/02 |
| 1234973 | 8/1968 | United Kingdom . | |
| 1129260 | 10/1968 | United Kingdom | A61K 3/78 |
| 1286183 | 11/1970 | United Kingdom | A61K 27/00 |
| 1247690 | 9/1971 | United Kingdom | C01B 33/18 |
| 2033915 | 10/1979 | United Kingdom | C08L 83/04 |

*Primary Examiner*—Thurman K. Page
*Assistant Examiner*—Sharon Howard
*Attorney, Agent, or Firm*—Sharon K. Severance

[57] ABSTRACT

Free-flowing granular compositions principally for use in treatment of gastric disorders comprise (A) titanium dioxide having a particle size within the range from 10 nanometers to 60 nanometers and a specific BET (nitrogen) surface area of at least 30 $m^2/g$ in combination with (B) an organopolysiloxane antifoam agent (for example a mixture of from 90 to 99 percent by weight of a polydiorganosiloxane and from 1 to 10 percent by weight of a finely-divided silica having a surface area to weight ratio of at least 50 $m^2/g$), (B) being present in a proportion of from 30 to 70 percent by weight calculated on the combined weight of (A) and (B). The compositions may contain from 40 to 60 percent of (B) based on the combined weight of (A) and (B). They may also contain an antacid or other medicament, glycerol, an effervescent agent and/or a disintegrant component.

12 Claims, No Drawings

ANTIFOAM COMPOSITIONS

This invention relates to novel compositions which are effective in reducing or preventing foaming in aqueous media and which are particularly adapted for use in the treatment of certain gastric disorders.

The use of organopolysiloxane compositions for the prevention and reduction of undesired foaming in manufacturing processes and domestic washing machines has long been known and widely employed. For example, British Patents 1 019 353 and 1 234 973 disclose processes for preparing antifoam compositions comprising reacting an organosiloxane polymer with a finely-divided filler in the presence of an acid condensation catalyst or a basic material respectively. British Patent No. 1 247 690 discloses an antifoam composition comprising a mixture of (A) a non-aqueous liquid, which may be a polydimethylsiloxane, and (B) the reaction product of a finely-divided inorganic filler with a dialkylamino organosilicone fluid. The operative fillers may be for example aluminium oxides, titanium dioxide or, more preferably, silica. In practice the proportion of filler employed in antifoam compositions is normally less than about 20% by weight and the product is employed as a viscous paste or as an aqueous emulsion.

It is also known that organopolysiloxane antifoam compositions have therapeutic uses. For example, they have been employed in veterinary practice to treat frothy bloat in ruminants. Such compositions have also found application in the treatment of gastric disorders in humans. One method of providing the compositions is as an emulsion, normally also containing an antacid. A generally more convenient dosage form requires that the composition be provided as a solid, for example as a tablet or as granules contained in a capsule of gelatin or similar soluble substance. Solid preparations of this type have been disclosed in for example British Patents 985 546 and 1 129 260 and more recently in U.S. Pat. Nos. 4,906,478 and 5,073,384. The said U.S. patents describe antigas or antiflatulent compositions obtained by combining simethicone and respectively calcium silicate or a water-soluble agglomerated maltodextrin. The simethicone ingredient is described in said U.S. Patents as a mixture of fully methylated linear siloxane polymers and silicon dioxide. Desirably, granular compositions should contain a high proportion of the active antifoam ingredient but at the same time should be free-flowing and be readily compressible into tablets. We have now found that such desirable properties can be realised by employing as a carrier for the antifoam composition certain titanium dioxides.

According to this invention there is provided a free-flowing granular composition comprising (A) titanium dioxide having a particle size within the range from 10 nanometres to 60 nanometres and a specific BET (nitrogen) surface area of at least 30 $m^2/g$ in combination with (B) an organopolysiloxane antifoam agent, (B) being present in a proportion of from 30 to 70 percent by weight calculated on the combined weight of (A) and (B).

Component (A) of the compositions of this invention is a titanium dioxide having a particle diameter within the range from 10 nanometres to 60 nanometres, preferably from 15 to 40 nanometres. The titanium dioxide should have a specific BET (nitrogen) surface area, measured according to DIN 66131 of at least 30 $m^2/g$ and preferably within the range from 35 to 100 $m^2/g$. Such titanium dioxides are known products and can be obtained by a pyrogenic process.

Any organopolysiloxane antifoam agent which is effective in breaking or otherwise controlling foaming in aqueous media may be employed as component (B) of the compositions of this invention. Such antifoam agents are well-known in the art and are described in, for example, G.B. 1 051 687, 1 051 688, 1 110 207 and 1 079 832. They are normally viscous or paste-like materials comprising a polydiorganosiloxane or, more preferably, a mixture of from 90 to 99% by weight of a polydiorganosiloxane with from 1 to 10 percent by weight of a finely-divided filler having a high (at least 50 $m^2/g$) surface area to weight ratio, for example a fume or precipitated silica or fume aluminium oxide. The polydiorganosiloxane component of the antifoam agent will normally have a viscosity within the range from 50 $mm^2/s$ to 5000 $mm^2/s$ at 25° C. However, polydiorganosiloxanes having viscosities outside this range may be employed. The silicon-bonded substituents in the polydiorganosiloxane are usually methyl groups but up to about 20 percent of the total substituents may be other than methyl, for example alkyl groups having from 2 to 6 carbon atoms. The polydiorganosiloxane present in the antifoam may or may not be end-stopped. Thus, they may be terminated with, for example, hydroxyl groups or end-stopped with triorganosiloxy groups such as trimethylsiloxy or dimethylvinylsiloxy groups.

Preferred for use in this invention are antifoams comprising a mixture of from 92 to 98 percent by weight of one or more polydimethylsiloxanes and from 2 to 8 percent by weight of a high surface area silica (at least 50 $m^2/g$). Having regard to its pharmaceutical acceptability the most preferred antifoam agent (B) is a mixture of polydimethylsiloxane and a high surface area silica known as Simethicone (USP XXII Monograph, pages 1248–9).

For most purposes it is desired that the compositions of this invention contain a high proportion of the antifoam component consistent with retaining their free-flowing granular nature. The preferred compositions of this invention are those which contain from 40 to 60 percent by weight of antifoam (B) based on the combined weights of (A) and (B). When the proportion of (B) exceeds about 60 percent by weight of the combined weights of (A) and (B) the composition becomes less free-flowing. This property can, however, be improved for such higher loadings of (B) by including in the composition a third component (C) which is a finely-divided silica having a surface area to weight ratio of at least 100 $m^2/g$ (BET nitrogen). This additional component (C) may be a fume or precipitated silica and may be the same as, or different from, any silica present in the antifoam compositions (B). When employed the additional component (C) is preferably present in an amount of from 0.5 to 8 percent by weight, based on the combined weights of (A), (B) and (C).

The compositions of the invention can conveniently be prepared by a two step process. As a first step the organopolysiloxane antifoam (B) is mixed with a portion of the titanium dioxide (A); the size of the portion, generally from about one half to about three quarters, being sufficient to provide a crumbly product which is only slightly greasy to the touch. A second step then involves adding the remainder of the titanium dioxide to the product of the first step to obtain a free-flowing granular composition. When high loadings of (B) render desirable or necessary the presence of silicon dioxide (C) this component can be added in admixture with the second portion of (A).

The compositions of this invention are particularly adapted for use in treating disorders of the gastric system, for example by acting to reduce foaming of the stomach contents. They may be employed in the granular or powdered form, for example filled into gelatine capsules, or in other dosage forms such as by compression into tablets. In a preferred embodiment of the invention the compositions are combined with pharmacologically active substances such as antacids for the treatment of hyperacidity for example aluminium hydroxide, magnesium carbonate, magnesium hydroxide, magnesium trisilicate, calcium carbonate and bismuth carbonate. Other pharmacologically-active substances which may be incorporated with the compositions of the invention include antibiotics, for example tetracycline, for the treatment or amelioration of ulceration or other stomach disorders. If desired the compositions may also be formulated with lubricants, flavours, binders and excipients, for example peppermint, sucrose, lactose, starch and milk solids. It has also been found advantageous to formulate the compositions of this invention with glycerol. It has been discovered that the presence of this additive in the compositions of this invention can reduce the time required to bring about a defoaming action in an aqueous system. An improvement in the defoaming activity can also be achieved by formulating the granular compositions as effervescent mixtures. Such formulation may be carried out by conventional means, for example by incorporating sodium bicarbonate or other compounds which release carbon dioxide such as glycin, lithium and potassium carbonates in association with one or more acids selected from citric, tartaric, boric, fumaric, cyclamic, sulphamic, adipic and nicotinic acids.

An improvement in the defoaming activity can also be achieved by formulating the granular compositions with disintegrants. Such formulation may be carried out by incorporating ingredients such as native and modified starches, crosslinked polyvinylpyrrolidone, cellulose and modified celluloses, alginic acids and derivative and gums.

The following Examples, in which the parts are expressed by weight, illustrate the invention.

EXAMPLE 1

A granular composition was prepared employing the following ingredients and procedure:

| | | |
|---|---|---|
| Simethicone USP | (1) | 165 parts |
| Pyrogenic $TiO_2$ | (2) | 133.5 parts |
| Pyrogenic $SiO_2$ | (3) | 1.5 parts |

(1) Mixture of 94 parts trimethylsiloxy-terminated polydimethylsiloxane (viscosity 3000 $mm^2/s$ at 25° C.) and 6 parts of high surface area silica
(2) Degussa P25, particle size <30 nm
(3) Particle size <50 nm (Aerosil 200, Degussa).

A portion of titanium dioxide (110 parts) was placed in a mixer and the total amount of Simethicone slowly added with high speed mixing until adsorbed. To the granular powder so obtained was then added with gentle mixing the remainder (23.5 parts) of the titanium dioxide and the pyrogenic silica. The resulting product was a free-flowing granular powder.

When the defoaming activity of the powder was measured as described in USP XXII, page 1249 (Simethicone Tablets monograph) a defoaming time of 15 seconds was obtained.

When the flow performance of the powder was measured as described in E.P., chapt V.5.F January 1991, a flowing time of 10 seconds was obtained with 100 g of product. Solid preparations comprising simethicone and agglomerated maltodextrin prepared by mixing the simethicone into the maltodextrin as disclosed in U.S. Pat. No. 5,073,384 were sticky and non-flowing and could not be tested by this procedure.

EXAMPLE 2

The following ingredients were employed to prepare an effervescent formulation

| | | |
|---|---|---|
| Simethicone USP | (1) | 85.5 parts |
| Pyrogenic $TiO_2$ | (2) | 59 parts |
| Pyrogenic silica | (3) | 1 part |
| Glycerol | | 4.5 parts |
| $NaHCO_3H_2O$ | | 7 parts |
| Citric acid | | 7 parts |

(1) Mixture of 94 parts trimethylsiloxy-terminated polydimethylsiloxane (viscosity 3000 $mm^2/s$ at 25° C.) and 6 parts of high surface area silica
(2) Degussa P25, particle size <30 nm
(3) Particle size <50 nm (Aerosil 200, Degussa).

The Simethicone and glycerol were mixed until a white homogeneous dispersion was obtained. This dispersion was then added with thorough mixing to a blend of 50 parts of the titanium dioxide and 5 parts of each of $NaHCO_3H_2O$ and citric acid. The remaining titanium dioxide (9 parts), colloidal silica (1 part), $NaHCO_3H_2O$ (2 parts) and citric acid (2 parts) were then added to the resulting composition with gentle (low speed) mixing to yield a granular, free-flowing powder.

When the powder was tested according to USP XXII, page 1249 (Simethicone Tablets monograph) a defoaming time of 5 seconds was obtained.

When the flow properties of the composition were measured as described in Example 1 a flow time of 10 seconds was obtained.

EXAMPLE 3

The following ingredients were employed to prepare a disintegrable composition

| | | |
|---|---|---|
| Simethicone USP | (1) | 81 parts |
| Colloidal $TiO_2$ | (2) | 59 parts |
| Colloidal $SiO_2$ | (3) | 1 part |
| Glycerol | | 9 parts |
| Explotab (TM) | (4) | 15 parts |

(1) Mixture of 94 parts trimethylsiloxy-terminated polydimethylsiloxane (viscosity 3000 $mm^2/s$ at 25° C.) and 6 parts of high surface area silica
(2) Degussa P25, particle size <30 nm
(3) Particle size <50 nm (Aerosil 200, Degussa).
(4) A proprietary disintegrant The Simethicone and glycerol were mixed as described in Example 2 and the resulting dispersion added slowly but with high mixing speed to a blend of $TiO_2$ (50 parts) and Explotab (10 parts). To this mixture were then added with gentle mixing the remainder of the ingredients. A granular, free-flowing powder was obtained which could be compressed into dosage size tablets.

When the powder was tested according to USP XXII, page 1249 (Simethicone Tablets monograph) a defoaming time of 5 seconds was obtained.

The flow properties of the composition were measured as described in Example 1 and a flow time of 10 seconds was obtained.

That which is claimed is:

1. A free flowing granular composition comprising (A) titanium dioxide having a particle size within the range from 10 nanometers to 60 nanometers and a specific BET (nitrogen) surface area of at least 30 $m^2/g$ in combination with (B) an organosiloxane antifoam agent comprising a mixture of from 90 to 99 percent by weight of a polydiorganosiloxane and from 1 to 10 percent by weight of a finely-divided filler having a surface area to weight ratio of at least 50 $m^2/g$; (B) being present in a proportion of from 30 to 70 percent by weight calculated on the combined weight of (A) and (B) .

2. A method for the preparation of a free-flowing granular composition comprising (A) titanium dioxide having a particle size within the range from 10 nanometres to 60 nanometres and a specific BET surface area of at least 30 $m^2$ g and (B) an organopolysiloxane antifoam agent wherein the method comprises the steps of (1) mixing a portion of the titanium dioxide (A) with the organopolysiloxane antifoam agent (B) and (2) adding to the product of step (1) the remainder of (A).

3. A composition as claimed in claim 1 wherein the filler is selected from the group consisting of a fume and precipitated silica.

4. A composition as claimed in claim 3 wherein the polydiorganosiloxane is a polydimethylsiloxane.

5. A composition as claimed in claim 1 wherein there is present from 40 to 60 percent of (B) based on the combined weight of (A) and (B).

6. A composition as claimed in claim 1 wherein the proportion of (B) exceeds 60% by weight and there is additionally present in the composition (C) at least 0.5% and up to 8% by weight based on the combined weight of (A), (B) and (C) of a finely-divided silica having a BET surface area of at least 100 $m^2/g$.

7. A composition as claimed in claim 1 which also contains a medicament for the treatment of gastric disorders.

8. A composition as claimed in claim 7 wherein the medicament is an antacid.

9. A composition as claimed in claim 1 which also contains glycerol.

10. A composition as claimed in claim 1 containing at least one component which causes effervescence when contacted with an aqueous liquid.

11. A composition as claimed in claim 1 which contains a disintegrant component.

12. A composition as claimed in claim 1 when prepared as a unit dose compressed tablet or capsule.

* * * * *